United States Patent [19]

Siemer et al.

[11] Patent Number: 5,185,024
[45] Date of Patent: Feb. 9, 1993

[54] APPLICATION OF AGRICULTURAL POLYAMMONIUM ACRYLATE OR POLYACRYLAMIDE HYDROGELS

[75] Inventors: Sidney R. Siemer, Fresno, Calif.; Louis L. Wood, Rockville; Gary J. Calton, Elkridge, both of Md.

[73] Assignee: Aqua Source Inc., Elkridge, Md.

[21] Appl. No.: 782,330

[22] Filed: Oct. 24, 1991

[51] Int. Cl.$^5$ .................. A01N 25/04; C05G 3/04
[52] U.S. Cl. ........................ 504/116; 71/27; 71/64.09; 71/DIG. 1; 504/320; 504/339
[58] Field of Search .............. 71/64.09, DIG. 1, 27, 71/65

[56] References Cited

U.S. PATENT DOCUMENTS

| | | | |
|---|---|---|---|
| 3,045,394 | 7/1962 | Coulter | 47/2 |
| 3,555,727 | 1/1971 | Jaquith | 47/2 |
| 3,950,159 | 4/1976 | Fox et al. | 71/11 |
| 4,051,086 | 9/1977 | Reid | 260/17.4 |
| 4,303,438 | 12/1981 | Zaslavsky et al. | 71/27 |
| 4,690,589 | 9/1987 | Owa | 405/263 |
| 4,756,738 | 7/1988 | Detroit | 71/27 |
| 4,797,145 | 1/1989 | Wallace et al. | 71/27 |

FOREIGN PATENT DOCUMENTS 62-273283 11/1987 Japan.

OTHER PUBLICATIONS

Tanaka, et al., Water-Retaining Agent for Agricultural Gels, Chemical Abstracts 109: 53920a, 1988.

*Primary Examiner*—Glennon H. Hollrah
*Assistant Examiner*—S. Mark Clardy
*Attorney, Agent, or Firm*—William S. Ramsey

[57] ABSTRACT

This invention discloses methods for manufacture and use of poly(ammonium acrylate) and polyacrylamide hydrogels in agricultural applications. Such hydrogels are applied to the soil or the plants by spraying. Spraying is advantageous over other methods of application, such as mixing with soil and broadcasting because of enhanced plant contact, evenness of distribution, and reduced labor. The gels are prepared for spraying by adding water to provide a readily deformable polymer which will pass through a spray apparatus. The hydrogels sprayed may include additives including micronutrients, maconutrients, pesticides, microbes, plant growth regulators, surfactants, and freezing point modifiers. Use of the hydrogels saves irrigation water and ameliorates salting of irrigated cropland. Sprayed hydrogels may also be used to protect crops from freezing and to protect foliage from desiccation.

5 Claims, No Drawings

APPLICATION OF AGRICULTURAL POLYAMMONIUM ACRYLATE OR POLYACRYLAMIDE HYDROGELS

BACKGROUND OF THE APPLICATION

1. Field of the Invention

This invention relates to methods for applying gels to agricultural soils and crops.

2. Description of Related Art

U.S. Pat. No. 3,045,394 discloses the application of 0.5% aqueous solutions of polyvinylpyrrolidone using sprays in order to prevent frost damage to plants.

U.S. Pat. No. 3,555,727 discloses solutions of molasses in combination with nonionic, anionic, and cationic emulsifiers which are applied with sprayers to prevent frost damage to plants.

U.S. Pat. No. 4,051,086 discloses a polyacrylamidepolysaccharide graft copolymer treated with glyoxal to increase its wicking action. The copolymer is applied by coating on sand or soil particles.

U.S. Pat. No. 4,303,438 discloses graft polymers formed from lignosulfate with acrylic acid or methacrylic acid which are used for improving soil structure. The graft polymers of this invention are said to be superior as "most of them can be diluted to any extent and sprayed without clogging of the nozzles."

U.S. Pat. No. 4,690,589 discloses forming a water-impermeable layer in soil using an aqueous solution of water-soluble poly(acrylic acid).

U.S. Pat. No. 4,797,145 discloses treating agricultural soil with mixtures of water soluble polyelectrolytes and polysaccharides.

Tanaka in Chemical Abstracts 109: 53920a, 1988, discloses a water retaining agent for agricultural soils composed of poly (ammonium)acrylate gel (PAA).

The prior art references do not disclose the process of applying insoluble hydrogels to agricultural soils or crops by spraying. In fact this property is not thought to be present in most polymers prepared for this purpose as it is cited as an unexpected and highly desirable property of graft polymers described in U.S. Pat. No. 4,303,438.

SUMMARY OF THE INVENTION

It is an object of this invention to provide a method for rendering hydrogels suitable for spraying.

It is an object of this invention to provide a method for using sprayable hydrogels to aid in retention of moisture in the soil and around plant roots.

It is an object of this invention to provide a method for reducing the amount of irrigation water needed to irrigate crops in areas of inadequate rainfall.

It is an object of this invention to provide a method for ameliorating the rate of salting of irrigated croplands.

It is an object of this invention to provide a method for making and applying sprayable hydropolymers containing incorporated pesticides, macronutrients or micronutrients, or crop regulator agents.

It is an object of this invention to provide a method for making and applying sprayable hydropolymers for protecting foliage from frost damage.

It is an object of this invention to provide a method for limiting transpiration and prolonging the survival of living plants stressed for water.

It is an object of this invention to provide a method for prolonging the period of pleasing appearance of cut plants or flowers.

It is an object of this invention to provide a method for reducing the amount of water and additives needed to grow irrigated crops.

Further objects, features, and attributes of the present invention will become apparent from the following description and appended claims.

The use of hydrogels as soil amendments and for treatment of crop foliage is well established. Polyacrylamide (PA), starch and polyacrylate gels have been described for this purpose. Use of hydrogels allows the retention of moisture in the soil or around the crop roots. This allows a substantial reduction in the use of irrigation water, a very important consideration in areas where water is in short supply. Reduction in the amount of irrigation water applied to cropland also has the benefit of slowing the build-up in the soil of salts carried by the water. In addition, many additives may be incorporated in the hydrogels, thereby effecting large savings in the amount of additives used, and consequently, in the amount of additives released to the environment. Such additives include micro-and macro-nutrients, and pesticides. An additional advantage is the slow release of these materials when applied in hydrogel form rather than in an aqueous solution. Coating the leaf surfaces of living or cut plants with hydrogels limit transpiration of water through the leaves, thus prolonging survival of living leaves in plants stressed for water, and prolonging the period of pleasing appearance of cut plants or flowers. Finally, hydrogels have been applied to the surface of crop plant to protect the foliage from frost damage. This application takes advantage of the high latent heat capacity of water to protect the plants.

Previously known methods of application of insoluble hydrogels include grinding of dried gels followed by broadcasting, mixing with soil, or filling holes in the soil with a mixture of gel and a soil mix. These methods are all discussed in the product literature of the various manufacturers and distributors of these materials over the last 40 years. These methods are all labor intensive, often involve an additional step in the planting process, and result in the ineffective use of the gel, or in too high a gel concentration near the roots, which causes excessive moisture retention and mold growth. No one has devised a method for economically incorporating these gels into the soil or applying such gels to foliage in an economic and effective fashion.

We have found that water-insoluble polyacrylamide (PA) and poly(ammonium)acrylate (PAA) gels may be applied by spraying after incorporation of sufficient water to render the hydrogel sufficiently deformable to pass through a spray apparatus. While dry, the gels are quite rigid. When wetted, however, the gel may swell up and incorporate 200 to 600 times its weight in water. At this point, the gel is greater than 99% by weight water. We have found that gels which contain 70% by weight or more water (preferably 85–99% by weight water) may easily be deformed such that they will pass through a spray apparatus. Reducing these particles to a smaller size prior to the addition of water allows them to quickly take up additional water. When these gels are placed in an aqueous solution, they readily take up additional water and may be sprayed, even at relatively high concentrations. Such gels may be sprayed into the air and hence onto the soil or onto foliage, or may be sprayed by use of a plow fitted with special attachments for spraying below the surface of the soil which allows the gel to be placed at a definite depth and concentration. The gels may be mixed with water in measured amounts and delivered via the nozzles on sprinkler systems.

We also have found that when the gels are 90% by weight water or more, the viscosity of the gel or gel water mixture may be adjusted by water addition such that seeds or bacteria may be suspended in the gel and subsequently sprayed on soil or plants.

DESCRIPTION OF THE PREFERRED EMBODIMENTS

Hydrogels may be manufactured by cross-linking polymers in the presence of water. Suitable polymers include polyacrylamide and poly(ammonium acrylate). Such hydrogels may include such additives as surfactants, plant micronutrients or macronutrients, pesticides including plant growth regulators, freezing point depressants, microbes, and colorants. In addition, seeds may be incorporated into the hydrogels.

Hydrogels typically are rigid and insoluble. We have found, however, that suitably hydrated hydrogels may be applied by spraying. It is speculated that rigid hydrogel particles become easily deformed and susceptible to flowing through spraying apparatus when suitably hydrated.

Hydrogels may be suitably hydrated by agitation in water until they are more than about 70% by weight water. To achieve this hydration within a short period of time it is preferable to reduce the particle size of the gel by grinding, extruding, chopping, macerating, blending, or other methods of particle size reduction. This process increases the surface area of the gel, thus providing a larger surface area which may be exposed to the hydrating liquid. The range of particle sizes from approximately 1 mm to 2 cm in diameter has been found useful in hydrating gels. The actual size is not important other than to reduce the time necessary for the gel particle to absorb proffered water. Preferably the hydrogel is hydrated until it is more than 95% by weight water, and most preferably until more than 99% by weight water. Of course, there are economic factors which dictate the percentage water which is optimum for specific applications. Preparations having higher percentages of water may be more expensive to apply than those with lower percentages of water.

A number of additives to the hydrogel have been recited above. These additives also may be incorporated in the water used for hydrating the hydrogel.

Suitably hydrated hydrogels may be applied by spraying from airplanes, from sprinklers, from mobile sprayers, or from permanently mounted spraying systems. They also may be applied by drip irrigation.

EXAMPLE 1

A poly(ammonium acrylate) (PAA) hydrogel was prepared as by Tanaka et al, Chemical abstracts 109: 53920a, 1988. Seven hundred g PAA hydrogel at 36% solids was prepared by mixing 200 g acrylic acid and 0.25 g N,N-methylenebis(acrylamide) with 190 ml of 28% by weight aqueous ammonia and 310 g water. An aliquot of 47.25 ml of a 2% by weight ammonium persulfate solution in water was added. The solution was allowed to stand overnight and the polymerization was complete. The resulting gel was allowed to swell in 800 ml water and greater than 76% by weight of the water was absorbed.

EXAMPLE 2

The gel prepared as in example 1, which contained 36% by weight solids, was added to 50 ml water at 0, 0.2, 0.4, and 0.8 g gel per 100 ml water. The mixtures were blended in a blender and 0.2 ml red food color was added to make the spray visible. The gels were sprayed through a SS8005 nozzle at 40 psi using $CO_2$ propellant onto paper. All concentrations except 0.8 g per 100 ml sprayed easily. A 2% by weight gel in water was sprayed at 40 psi pressure through a TK5 flood jet nozzle.

TWEEN 20 surfactant was added to 1% by weight gel in water at 0.1% by weight TWEEN 20 or 0.24% by weight TWEEN 20 and sprayed with a flood D-4 nozzle at 30 psi. A finer spray with smaller droplets closely spaced was observed when TWEEN 20 was included in the suspension. TWEEN 20 is a trademark owned by ICI Americas for polymeric surfactants made of polyoxyethylene sorbitan mono-lauroate.

EXAMPLE 3

Polyacrylamide gels (PA) used were sold under the trademark CRYSTAL SOIL, a trademark for PA belonging to Crystal Co., St. Louis, Mo., and MOISTER MIZER, a trademark for PA belonging to Multiple Concepts, Chattanooga, Tenn. In each case PA was macerated in a blender. Water was placed in a blender, filling it about half way, and while blending at low speed, PA was added to 5-10% by weight. The gel was liquified at high speed 45-60 seconds and a sample poured into a petri dish and examined for visible globules. Lack of visible globules indicated a sprayable mixture. Visible globules were removed by additional blending. Water was added to a 1% by weight gel concentration and the gel was sprayed.

EXAMPLE 4

PAA gel prepared as in Example 1 was used to treat two year old turf (variety Fescue) located near Fresno, Calif. in late June and early July, 1991. The weather was hot and dry, with daytime temperatures reaching 105°-112° F. There were three replicates per treatment. Replicate sets were arranged in blocks and each plot was surrounded by an untreated area. Plots were 7.5 feet by 3.3 feet for the low rate treatments (0 and 200 pounds polymer per acre) and 3.8 feet by 3.3 feet for the high rate treatment (1300 pounds polymer per acre). Polymer was applied as 2% by weight concentrated material in water using a $CO_2$ pressurized backpack sprayer and handgun. Polymer was applied with and without TWEEN 20 surfactant at a concentration of 0.25% by weight.

The sprays were applied as in Table 1. After application one inch of sprinkler irrigation was applied to the turf over a 4 hour period. Three days later, one additional irrigation of 0.25 inch was made.

The treatments were evaluated 10 days after application following a week of hot daytime temperatures. The condition of the turf was evaluated using a rating scale of 1 to 3. A rating of 1 indicated turf stressed to the wilting point and brownish-green in color. A rating of 3 indicated normal, lushly growing turf, dark green in color. A rating of 2 was intermediate.

The results are in Table 1. All the polymer treatments enhanced preservation of the turf, compared to the untreated controls. Application of polymer at the rate of 1300 pounds polymer per acre was more effective than at 200 pounds of polymer per acre. Use of surfactant improved turf quality at low levels while at high levels of polymer the turf score was higher and no systemic effect could be seen. Treatments containing surfactant were observed to have enhanced wetting of the turf, to film rather than clump on the foliage, and to have enhanced movement of the gel through the thatch and into the soil.

TABLE 1

| Treatment | Rate of Application Pounds Polymer per Acre | Turf Quality |
|---|---|---|
| 1. PAA | 200 | 2.2 |
| 2. PAA + TWEEN 20 | 200 | 2.3 |
| 3. PAA | 1300 | 2.8 |
| 4. PAA + TWEEN 20 | 1300 | 2.8 |
| 5. Control | — | 1.5 |

End of TABLE 1

EXAMPLE 5

The effect of spraying PAA hydrogel with and without TWEEN 20 on pinto bean seeds or on the surface of the sand after planting the beans was determined. The pinto beans were grown in sand in 10 oz. plastic cups with holes in the bottom. Four beans were planted in each cup and there were four replicates of each treatment. The treatments involving hydrogels were sprayed using a $CO_2$ pressurized hand sprayer with a flood D-4 nozzle at 20 psi. When the hydrogel was sprayed on the beans, the beans were then planted. When the hydrogel was sprayed on the soil, the beans were planted and covered with soil, which was then sprayed. All treatments were watered with 50 mls on the day of planting and with 25 mls on the 10th day. The "regular water" treatment was also watered with 25 mls on the 5th and 9th days. The beans were grown under a fluorescent light. The test was terminated on the 21st day.

TABLE 2

| Treatments of Pinto Beans Grown in Sand |
|---|
| 1. No hydrogel |
| 2. No hydrogel, regular water |
| 3. 1% hydrogel, 0.1% TWEEN 20 sprayed on soil after planting |
| 4. 1% hydrogel, 0.1% TWEEN 20 sprayed on beans |
| 5. 1% hydrogel, 0.24% TWEEN 20 sprayed on soil after planting |
| 6. 1% hydrogel, 0.24% TWEEN 20 sprayed on beans |

End of Table 2

Beans in treatment 4 were the first to emerge on day 2. Beans in treatment 3 and 6 emerged on day 4. The remaining beans emerged on day 7.

On day 21, plants in treatment 2 had the most vigorous growth of all treatments. The growth in treatments 1 and 4 was very poor. The growth in treatments 3, 5, and 6 was more vigorous than that in treatment 1 but less vigorous than that of treatment 2.

This shows the effect of hydrogel in stimulating the germination and emergence of beans. None of the treatments allowed growth equal to that of abundant water. The treatments with hydrogel and a the high level of surfactant sprayed on either the beans or the soil and the treatment with hydrogel and the low level of surfactant sprayed on the soil, however, were superior to the treatment lacking gel but receiving a similar amount of water.

It will be apparent to those skilled in the art that the examples and embodiments described herein are by way of illustration and not of limitation, and that other examples may be utilized without departing from the spirit and scope of the present invention, as set forth in the appended claims.

We claim:

1. The method of applying poly(ammonium acrylate) or polyacrylamide hydrogels to agricultural soils or crops comprising the steps:
   1. forming a water-insoluble rigid hydrogel by cross-linking a polymer comprising poly(ammonium acrylate) or polyacrylamide,
   2. reducing the rigid hydrogel particle size to about 1 mm to about 2 cm in diameter,
   3. hydrating the hydrogel particles to about 85-99% by weight water, and
   4. applying the hydrated hydrogel particles by spraying.

2. The process of claim 1 wherein the hydrated hydrogel contains greater than about 90% by weight of water.

3. The process of claim 1 wherein the hydrated hydrogel contains about 95% by weight or greater of water.

4. The process of claim 1 wherein surfactant is included in the hydrogel.

5. The method of applying a rigid hydrogel of poly(ammonium acrylate) or polyacrylamide to agricultural soils or crops comprising the steps:
   1. reducing the rigid hydrogel of poly(ammonium acrylate) or polyacrylamide particle size to about 1 mm to about 2 cm,
   2. hydrating the rigid hydrogel of poly(ammonium acrylate) or polyacrylamide particles to about 85-99% by weight water, and
   3. applying the hydrated hydrogel of poly(ammonium acrylate) or polyacrylamide particles by spraying.

* * * * *